United States Patent
D'Silva

[11] Patent Number: 5,353,113
[45] Date of Patent: Oct. 4, 1994

[54] SINGLE AND MULTIPLE RADIATION TRANSPARENT AFTERGLOW ELECTRIC DISCHARGE DETECTOR SYSTEMS

[75] Inventor: Arthur P. D'Silva, Ames, Iowa

[73] Assignee: Cetac Technologies Incorporated, Omaha, Nebr.

[21] Appl. No.: 91,264

[22] Filed: Jul. 15, 1993

[51] Int. Cl.⁵ .................................... G01N 21/66
[52] U.S. Cl. .................................... 356/311
[58] Field of Search ............... 356/311, 313, 314, 316, 356/417

[56] References Cited

U.S. PATENT DOCUMENTS

| | | | |
|---|---|---|---|
| Re. 33,415 | 10/1990 | Jelic | 313/609 |
| 2,901,625 | 8/1956 | Friedman et al. | 250/435 |
| 2,943,223 | 6/1960 | Fay | 313/201 |
| 3,390,351 | 6/1963 | Bell | 331/94.5 |
| 3,612,686 | 10/1971 | Braman et al. | |
| 3,685,911 | 8/1972 | Dahlquist et al. | |
| 3,900,237 | 8/1975 | Marcucci | 316/20 |
| 4,001,624 | 1/1977 | Cosco et al. | 313/185 |
| 4,028,617 | 6/1977 | Kamo et al. | 324/33 |
| 4,225,235 | 9/1980 | Anderson et al. | 356/316 |
| 4,479,075 | 10/1984 | Elliott | 315/111.21 |
| 4,509,855 | 4/1985 | Gay | 356/72 |
| 4,648,951 | 3/1987 | Maya | 204/157.2 |
| 4,762,402 | 8/1988 | Michon et al. | 350/370 |
| 4,789,783 | 12/1988 | Cook | 250/379 |
| 4,801,209 | 1/1989 | Wadlow | 356/417 |
| 4,853,938 | 8/1989 | Neubauer et al. | 372/65 |
| 4,877,997 | 10/1989 | Fein | 313/634 |
| 4,898,465 | 2/1990 | Crawford et al. | 356/311 |
| 5,062,116 | 10/1991 | Christensen | 372/61 |
| 5,117,150 | 5/1992 | Schwartz et al. | 313/112 |
| 5,126,676 | 6/1992 | Huston | 324/464 |
| 5,186,323 | 12/1992 | Purtschert et al. | 356/313 |

OTHER PUBLICATIONS

An $M_9F_2$–No Ion Chamber with $O_2$ Gas Filter as a detector of solar Hlyman-$\alpha$ Radiation; J. . . E Sci. Instrum; vol. 13, No. 11, Nov. 1980.

Primary Examiner—F. L. Evans
Attorney, Agent, or Firm—James D. Welch

[57] ABSTRACT

An afterglow electric discharge detector system for use in analysis of samples is disclosed. Fabrication is predominately from machined radiation transparent material such as crystalline magnesium or lithium fluoride.

10 Claims, 1 Drawing Sheet

SINGLE AND MULTIPLE RADIATION TRANSPARENT AFTERGLOW ELECTRIC DISCHARGE DETECTOR SYSTEMS

TECHNICAL FIELD

The present invention relates to afterglow detector systems and more particularly to radiation transparent single and multiple afterglow electric discharge detector systems which minimize contamination of samples detected therein and facilitate detection and analysis of produced sample identifying radiation.

BACKGROUND

The use of metastable afterglow species to excite sample atoms, molecules and/or fragments etc. so that identifying radiation is emitted thereby when they relax is known. Existing systems for use in practicing sample analysis techniques which utilize metastable afterglow species, however, typically provide for formation of said metastable afterglow species within a tube or the like which is made from oxygen containing materials. Continuing, formation of metastable afterglow species inside said tube or the like is typically by electric discharge. This is mentioned as said electric discharge commonly causes oxygen atoms and molecules etc. to be sputtered from the inner surface of said tube or the like. The presence of said oxygen atoms and molecules etc. can lead to sample analysis complicating oxygen contamination. It should also be appreciated that use of tubes or the like made from, or lined with, other materials can likewise lead to sample contamination by elements other than oxygen contained in, and sputtered from, said other materials during electric discharge.

It should be appearant that when sample identifying radiation, originating when energy released from metastable afterglow species interacts with closely situated sample molecules, atoms and/or other fragments is to be analyzed said radiation must escape from the tube or the like in which said metastable afterglow species and sample are contained and enter a radiation analysis system detector. This requires that said tube or the like of said sample excitation detector system provide, at a minimum, a window area which is transparent to said radiation. Said window must also be located so that it can conveniently couple said escaping sample identifying radiation to said radiation analysis system detector. Design of sample excitation detector systems must therefore be undertaken with radiation analysis system geometry in mind. This is to be understood in view of the fact that different radiation analysis systems have different geometries thereby making inter-changability of sample excitation detector systems there-amoungst difficult.

It is also mentioned that when electric discharge takes place inside an electric discharge chamber, carbon is formed Therein. Carbon can build-up inside an electric discharge system and serve to adversely effect sample analysis results mediated thereby.

In view of the above it should be appreciated that a system for generating metastable afterglow species which is made at least in part from a non-oxygen containing material, which non-oxygen containing material is essentially transparent to radiation emitted by sample atoms, molecules and/or fragments etc. excited inside said system by interaction with energy released from said metastable afterglow species created therein, would be of great utility. Not only could oxygen contamination of sample be avoided, but as well, said system would be relatively easy to design for use with various radiation analysis detector systems. The later attribute resulting because essentially the entire system would allow sample identifying radiation produced therein to escape. As alluded to above, conventional sample excitation detector systems provide only a relatively small window through which sample identifying radiation can escape. In addition, if the non-oxygen containing material is one which contains atoms which easily combine with carbon to form a volatile compound, carbon developed during metastable species creating electric discharge might be easily removed from the electric discharge system in the form of a volatile compound of carbon and atoms sputtered from said non-oxygen material during said electric discharge, instead of depositing inside said tube or the like in which electric discharge takes place. This would provide obvious utility and allow easy cleaning of the system.

A search of Patents has provided a patent, U.S. Pat. No. 2,943,223 to Fay. This Patent describes an elongated hollow dielectric member with closure means at each end thereof, one of which is transparent to radiation produced inside thereof by electric discharge between two elongated electrodes present therein. Gas entry and exit means are also present at opposite extents of the elongated hollow dielectric member.

Another patent, U.S. Pat. No. 4,225,235 to Anderson et al. describes an elongated sample introduction system for flameless emission spectroscopy comprising a reaction chamber which has means for aspirating a sample solution thereinto at one end thereof. Aspirated sample is subjected to energy present in microwave discharge generated metastable species formed from gas injected simultaneous with said aspirated sample. Light collection and focusing optics are also described for use in focusing light emitted by excited sample into a detection system.

A Patent to Braman, U.S. Pat. No. 3,612,686 describes a method and system for spectrochemical analysis of a subject gas introduced by a carrier gas flow into an elongated analysis chamber, which elongated analysis chamber has electrodes present at each end thereof. During use a continuous direct current discharge is typically applied to the electrodes to sustain a plasma in The carrier gas. It is mentioned that the carrier gas utilized should have a high ionization potential, preferably higher than any of the components of a subject gas to be detected. The analysis chamber is described as being comprised of an electrically insulating material through which can pass the frequencies of radiation expected to De radiated. Pyrex brand glass and quartz are given as examples of suitable electrically insulating materials. Gas entry and exit means are present at opposite ends of said elongated analysis chamber.

A Patent to Dahlquist et al., U.S. Pat. No 3,685,911 describes a capillary arc plasma device comprised of a straight tubular passageway with an anode at one end thereof and a and cathode at an opposite end thereof, which cathode is shielded from the anode end of the passageway to minimize transmission of light from the cathode through the passageway and enable end-on spectrometric observation of an arc in the passageway. During use electric discharge is caused to occur between the anode and cathode and sample is entered to the discharge. The use of a lithium fluoride window is identified as a means to allow detection of radiation produced by interaction between the electric discharge and the sample at wavelengths as short as about eleven-hundred (1100) Angstroms.

U.S. Pat. No. 5,117,150 to Schwartz et al. describes a deuterium lamp with a quartz glass bulb for spectral analyzers. At least the portion of the quartz glass bulb through which the radiation passes is provided on its outer surface with a multiple interference filter. The multiple interference filter, which is vapor-deposited, is comprised of alternating aluminum oxide and silicon dioxide or magnesium fluoride. The purpose of the multiple interference filter is to reduce radiation noise Another Patent, U.S. Pat. No. Re. 33,415 to Jelic describes a double-bore capillary tube gas discharge lamp with an envelope window transparent to short wavelength light. The envelope window is identified as being made of magnesium fluoride.

A Patent to Crawford et al., U.S. Pat. No. 4,898,465 describes a gas analyzing apparatus comprising a quartz tube is housed in a body made from a material with extremely low electrical conductivity and thermal coefficient of expansion, but with high thermal conductivity and machinability. Boron nitride is mentioned as a suitable material. The quartz tube has anode and cathode electrodes at opposite ends thereof for causing a D.C. glow discharge during use. Said quartz tube is also bent so that said anode and cathode are non-colinear. Contaminates entered with sample gas are caused to impinge on the quartz tube at the bend therein and are deposited thereat. A photodetector is coaxially sighted with the downstream leg of the bent pathway. Errors due to fogging of the pathway over time are thus eliminated.

A Patent to Christensen, U.S. Pat. No. 5,062,116 describes a halogen-comparable high-frequency discharge apparatus. Discharge tubes formed of metal fluoride glasses, (note that glasses are amorphous), are used in apparatus for emitting high frequency laser and fluorescent light. The use of metal fluorides glasses serves to make the discharge tubes resistant to corrosion from halogen-containing gas mixtures subjected to high frequency excitation in the apparatus.

Analysis of the Patents cited shows that a need remains for an afterglow electric discharge detector system for use in sample excitation which at once:
  a. allows excitation of sample in an electric discharge tube or the like made of, or lined with, a selected material,
  b. is predominantly made from a material which is transparent to sample identifying radiation, and
  c. is preferably made from a material which can combine with carbon to form volatile compounds so that carbon formed during metastable species forming electrical discharge can be easily removed from the system.

Such a sample excitation system should optionally provide multiple separate electrical discharge pathway(s) which present various materials within which an electrical discharge can occur. Said multiple electrical discharge pathways allowing analysis of samples which contain elements present in other electrical discharge pathways without contamination thereof by sputtered atoms and molecules etc. In addition, the material from which the afterglow electric discharge detector system is constructed should be easily machinable to allow formation thereof into desired configurations.

DISCLOSURE OF THE INVENTION

The present invention, (an afterglow electric discharge detector system), in its most basic form, provides that a block of radiation transparent crystalline magnesium fluoride or crystalline lithium fluoride should be machined to include at least one hole from one side thereof therethrough to another side Thereof. (It is noted that the word "block" can include other than rectangular shapes). The ends of said machined hole at the sides of said block of crystalline magnesium or lithium fluoride being sized for, and each being fitted with an electrode. In addition means for allowing a sample and carrier gas to be caused to flow through said machined hole between said electrodes, in what is an effective afterglow electrical discharge region, are present. Said means for allowing a sample and carrier gas to be caused To flow through said afterglow electrical discharge region can be entry and exit ports, each being positioned centrally between said electrodes so that said entered sample and carrier gas does not pass through an electrode when entering or exiting said afterglow electrical discharge region in said hole between said electrodes. However, said means for allowing sample and carrier gas to flow through said afterglow electrical discharge region can, alternatively, pass through one or both electrodes. In addition, the present invention can have highly thermal conductive material such as diamond, deposited to a portion of the outer surface of said block of crystalline magnesium or lithium fluoride to aid with heat removal therefrom during use, and might have a lining of a material other than magnesium or lithium fluoride on the inner wall of the machined hole between said electrodes in the afterglow electrical discharge region.

The present invention can also be embodied so as to include multiplicity of machined holes through said block of crystalline magnesium or lithium fluoride, with one or more or said machined holes being lined with material other than magnesium or lithium fluoride. For instance red glass tubing inserted into a machined hole might effect such a lining.

In use a sample in a carrier gas, (said carrier gas typically being helium), is caused to flow through a machined hole between associated electrodes and an electrical discharge is caused to occur between said electrodes. (Note, that more than one machined hole can have commonly excited electrodes or a machined hole can be provided independently excited electrodes). During use electrical energy is typically, but not necessarily, applied intermittently and at up to fifty (50) watts or more at approximately three-hundred (300) KHZ. During said intermittent electrical discharge metastable species are formed from carrier gas molecules, and during the period in which electrical discharge does not occur energy released from said metastable species interacts with sample molecules, atoms and/or other fragments such that excitation thereof occurs. When said excited sample molecules, atoms and/or other fragments relax they emit radiation of a characteristic identifying wavelength. Said radiation passes through the crystalline magnesium or lithium fluoride and can then be analyzed by a detector in a radiation analysis system.

it is important to understand that crystalline magnesium fluoride is transparent to wavelengths between one-hundred-twenty (120) nanometers and one-thousand (1000) nanometers and that lithium fluoride is transparent to wavelengths between one-hundred-ten (110) and one-thousand (1000) nanometers. As the present invention is made from a block of machined crystalline magnesium or lithium fluoride sample identifying radiation of wavelengths in said ranges, originating from relaxing sample molecules, atoms and/or other fragments in a machined hole therein, can pass therethrough unattenuated over a majority of the body of the present invention. Only those regions of the invention at which electrodes are present or which a highly thermal conductive material is present being non-transparent or at least less transparent. It is mentioned that a lining of a material other than magnesium or lithium fluoride on the inner wall of a machined hole, if thin enough, might have only minimal effect on the escape of radiation from relaxing sample molecules, atoms and/or other fragments in the effective afterglow electrical discharge region. It should then be appreciated that coupling said emitted radiation to a radiation analysis system detector can typically be easily effected, as alignment with a small window of transparent material at some fixed location on an afterglow electric discharge detector system is not required. It is emphasized that conventional systems for performing a similar function typically provide only small windows of radiation transparent material, and said small windows can be difficult to align with entry ports to detectors in radiation analysis systems.

It is also to be understood that metastable species producing electrical discharge inside a machined hole through a block of crystalline magnesium or lithium fluoride can cause fluorine atoms or molecules to be freed by sputtering. Said free fluorine atoms or molecules can serve to contaminate a sample with fluorine just as sputtered oxygen atoms from a quartz discharge tube, for instance, can contaminate a sample with oxygen. It is for this reason that it is within the scope the present invention to provide multiple machined holes through said radiation transparent crystalline magnesium or lithium block and provide a lining to the inner wall of some of said holes made of other than magnesium or lithium fluoride. For instance, as mentioned, a red glass might tube be used to line the inner surface of one such hole. If a sample to be analyzed might contain fluorine atoms which are to be detected, a portion of said sample can be excited in said red glass lined hole afterglow electric discharge region, for instance. When more than one effective afterglow electrical discharge region is provided electrical energy it is also possible to provide waveguides to direct radiation from one or more thereof to separate radiation analysis system detectors. As well, inner wall linings and waveguides can be used with single machined hole afterglow electric discharge systems.

When sputtered fluorine atoms or molecules will not present a sample analysis contamination problem it is to be understood that the presence thereof actually provide a benefit. It is well known that carbon is a by-product of electrical discharge. In conventional electrical discharge systems carbon deposits inside electrical discharge tubes can build-up and serve to degrade sample analysis results mediated by sample excitation in said electrical discharge tube. However, in the presence of fluorine atoms or molecules, carbon forms volatile fluorocarbons. Such volatile compounds do not deposit in electrical discharge systems and quickly flow therefrom along with the sample containing carrier gas. In fact, an electrical discharge system made from crystalline magnesium or lithium fluoride can be sputtered clean by flowing, for instance, sample-free argon gas therethrough during an electrical discharge.

The present invention is then found in the use of a radiation transparent crystalline block of magnesium or lithium fluoride into which are machined afterglow electrical discharge region(s), (i.e. holes), in combination with sample and carrier gas entry and exit means, electrical discharge effecting electrodes and electrical energy sources, and perhaps in combination with highly thermal conductive films deposited on portions of the outside of said radiation transparent, crystalline block of magnesium or lithium fluoride block and/or perhaps non-magnesium or lithium fluoride containing material linings in said afterglow electrical discharge regions.

The present invention will be better understood by reference to the Detailed Description Section of this Disclosure conjunction with the Drawings.

DETAILED DESCRIPTION

Figure 1:
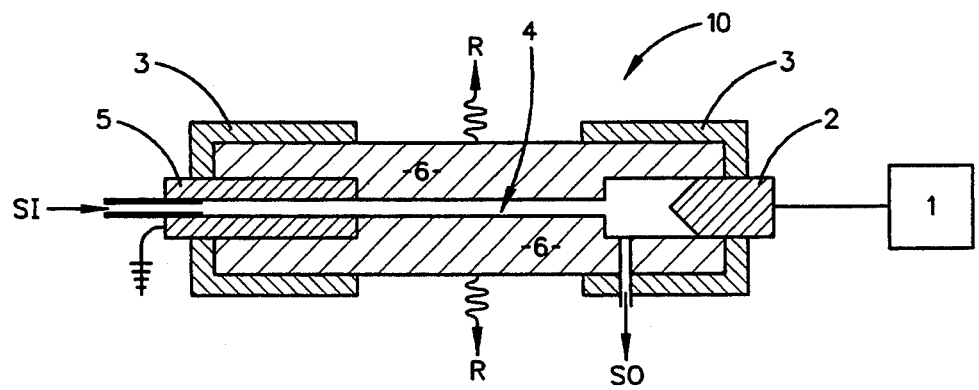
FIG. 1 shows a cross-sectional view of one embodiment of an afterglow electric discharge detector system contained in a block of machinable radiation transparent material.

Turning now to the Drawings, there is shown in FIG. 1 a cross sectional view of a first embodiment (10) of the present invention comprising a radiation transparent crystalline magnesium or lithium fluoride block (6) with electrodes (2) and (5) at the ends of a hole (4) machined therethrough, said hole (4) machined between said electrodes (2) and (5) forming an afterglow electrical discharge region therein. Optional highly thermal conductive heat transfering films (3), typically made from diamond, are shown deposited at the outer ends of the block of magnesium or lithium fluoride. Sample and carrier gas entry means (SI) are shown passing through electrode (5) and sample and carrier gas exit means (SO) are shown located centrally from electrode (2). During use sample containing carrier gas is caused to flow into sample and carrier gas entry means through electrode (5) and out of exit means (SO). Electrode (5) is, during use, typically grounded, and intermittent electrical energy is applied to electrode (2) from electrical energy source (1). Said intermittent electrical energy typically, but not necessarily, is applied at up to fifty (50) watts or more and at a frequency of approximately three-hundred (300) KHZ. The resulting electrical discharge creates metastable species from carrier gas molecules in the afterglow electrical discharge region formed by machined hole (4) between electrodes (2) and (5). During periods when electrical discharge is not effected, energy released from said metastable species interacts with sample molecules, atoms and/or other fragments to the end that sample molecules, atoms and/or other fragments become excited. When said sample molecules, atoms and/or other fragments relax radiation "R" of an identifying wavelength is emitted. It will be appreciated that said radiation will pass from the body of the present invention over a large portion thereof, if said radiation is in the range at which magnesium or lithium fluoride is transparent to radiation. As mentioned in other sections of this Disclosure, said range is one-hundred-twenty (120) to one-thousand (1000) nanometers for crystalline magnesium fluoride and one-hundred-ten (110) to one-thousand (1000) nanometers for crystalline lithium fluoride.

Figure 2:
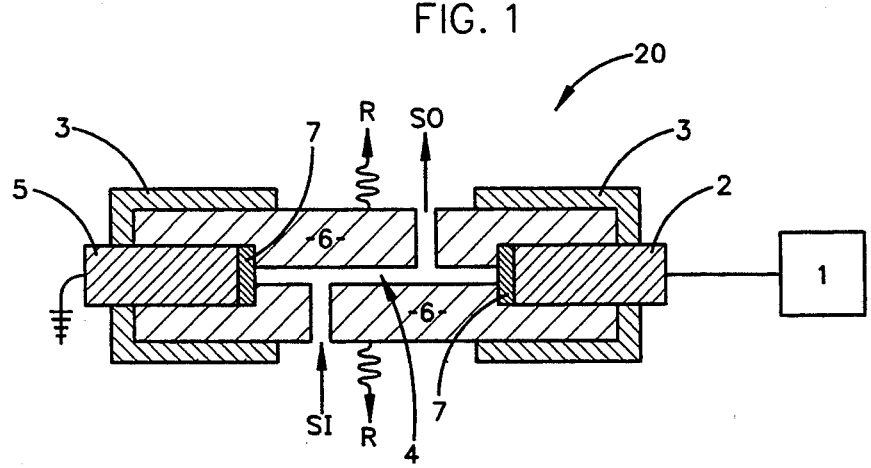
FIG. 2 shows a cross-sectional view of a modified embodiment of an afterglow electric discharge detector system contained in a block of machinable radiation transparent material.

Turning now to FIG. 2, there is shown a cross sectional view of a modified embodiment (20) of the present invention. It will be noted that a block of radiation transparent crystalline magnesium or lithium fluoride (6) is again shown as are optional heat transfering films (3). Also shown are electrodes (2) and (5). The sample and carrier gas entry means (SI) in the second embodiment, however, is not through the electrode (5), but rather via a machined port located centrally from said electrode Sample and carrier gas exit means (SO) is likewise machined at a location centrally located with respect to electrode (2). Note that sample and carrier gas exit means (SO) could be project from the same side of the block of crystalline magnesium or lithium fluoride at which the sample and carrier gas entry means (SI) is present. Shown also are magnesium or lithium fluoride disks (7) at the center-most ends of electrodes (2) and (5). These serve to seal said electrodes (2) and (5) against contact with sample and carrier gas during use. Operation of the second embodiment is similar to operation of the first embodiment. Electrical energy is intermittently applied to electrode (2) from electrical energy source (1) to form metastable species in the afterglow electrical discharge region in machined hole (4) between electrodes (2) and (5), which electrode (5) is typically grounded.

Figure 3:
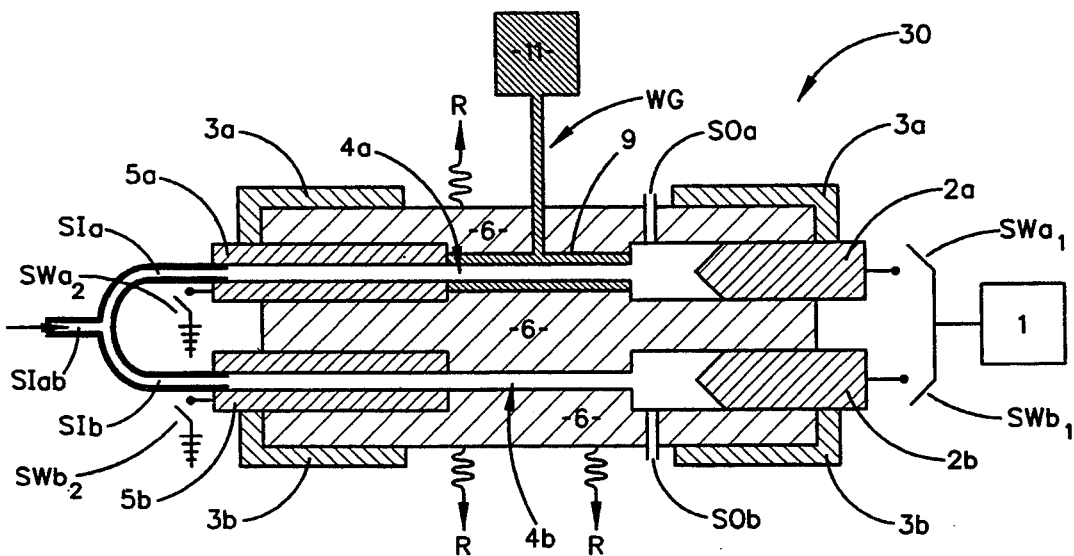
FIG. 3 shows a cross-sectional view of a multiple afterglow electric discharge detector system contained in a single block of machinable radiation transparent material.

Turning now to FIG. 3, there is shown a cross sectional view of a third embodiment (30) of the present invention. Said third embodiment (30) being a dual discharge system. Said third embodiment is demonstrated as essentially a double version of the first embodiment (10), with a lining of a material other than magnesium or lithium fluoride (9) present on the inner wall of machined hole (4a) in the afterglow electric discharge region between electrodes (2) and (5). Note that the subscripts "a" and "b" are used to distinguish the identifying numerals in the two afterglow electric discharge detector systems present in said block of magnesium or lithium fluoride (6). During use sample in carrier gas is caused to flow into port (SIab), split into two parts and flow in part through machined hole (4a) and in part through machined hole (4b). Electrical energy is intermittently selectively applied to electrodes (2a) and/or (2b) as described with respect to the first two embodiments. Switches, (SWa) and (SWb) can be present to allow energization of only electrode (2a) or only electrode (2b) if desired during use. Each switch provides a contact for coupling electrical energy to associated electrodes (2a) or (2b), (i.e. contacts (SWa1) and (SWa2) respectively). Grounding path providing switches at electrodes (5a) and (5b), (i.e. contacts (SWa2) and (SWb2) respectively) can also be present to allow selective grounding of electrodes (5a) and (5b). Note that a waveguide (WG), (typically of fiber optic construction), is also shown as present. When present it serves to direct sample identifying radiation developed in afterglow electrical discharge region in hole machined (4a) to a radiation analysis system detector (11). This can be necessary when both electrodes (2a) and (2b) are energized simultaneously if it is desired to separately detect the radiation produced by sample molecule, atom and/or other fragment relaxation in afterglow electrical discharge region in machined hole (4a). As described in the Disclosure of the Invention Section of this Disclosure, said dual discharge system allows avoidance of fluorine contamination of sample entered to afterglow electrical discharge region in machined hole (4a), which is lined with non-magnesium or lithium fluoride containing material (9). It is to be understood that said third embodiment could utilize sample and carrier gas entry means (SI) and exist means (SO) similar to that shown in FIG. 2 and be within the scope of the present invention. Other functionally similar configurations are within the scope of all embodiments. That is, the focus of the present invention is on the predominant use of a radiation transparent, crystalline magnesium or lithium fluoride block in which are machined afterglow electric discharge detector system regions. Specific geometries shown in FIGS. 1-3 are therefore to be considered demonstrative and not limiting. Functionally equivalent configurations are to be considered equivalent for the purposes of Claim interpretation.

It is noted that the inner diameter of holes machined into blocks of magnesium or lithium fluoride can be a relatively small diameters, (e.g. one-half (0.5) milimeter). This allows better concentration of afterglow excitation electric discharge energy than is possible in conventional electric discharge tubes or the like which typically provide inner diameter afterglow electric discharge regions with diameters on the order of one (1.0) milimeter.

Finally, while the present Disclosure has used machinable crystalline magnesium or lithium fluoride as examples of acceptable materials for use in the practice of the present invention, it is to be understood that use of functionally equivalent materials are also within the scope of the present invention. The phrase "machinable radiation transparent material" is to be understood to be sufficiently broad to encompass any functionally equivalent material.

Having hereby disclosed the subject matter of the present invention, it should be obvious that many modifications, substitutions, and variations of the present invention are possible in light of the teachings. It is therefore to be understood that the invention may be practiced other than as specifically described, and should be limited in breadth and scope only by the Claims.

I claim:

1. An afterglow electric discharge detector system of the type including an afterglow electrical discharge region with electrodes positioned with respect thereto so as to allow creation of an electric discharge in said afterglow electrical discharge region when electrical energy is applied to said electrodes, which also includes means for allowing sample and carrier gas to be caused to flow through said afterglow electrical discharge region; in which the improvement comprises the construction of said afterglow electric discharge detector system predominantly from a block of machinable radiation transparent material, into which is machined at least one hole, said hole serving to form an afterglow electrical discharge region.

2. An afterglow electric discharge detector system as in claim 1 in which the means for allowing sample and carrier gas to be caused to flow through said afterglow electrical discharge region comprise ports located such that sample and carrier gas do not flow through the electrodes.

3. An afterglow electric discharge detector system as in claim 1 in which the means for allowing sample and carrier gas to be caused to flow through said afterglow electrical discharge region requires said sample and carrier gas to flow through at least one electrode.

4. An afterglow electric discharge detector system as in claim 1 which further comprises highly thermal conductive material over at least a portion of the outer surface thereof.

5. An afterglow electric discharge detector system as in claim 1 in which the inner wall of the hole machined into the block of machinable radiation transparent material is lined.

6. An afterglow electric discharge detector system as in claim 1 in which the block of machinable radiation transparent material is selected from the group consisting of crystalline magnesium fluoride and crystalline lithium fluoride.

7. An afterglow electric discharge detector system of the type including an afterglow electrical discharge region with electrodes positioned with respect thereto so as to allow creation of an electric discharge in said afterglow electrical discharge region when electrical energy is applied to said electrodes, which also includes means for allowing sample and carrier gas to be caused to flow through said afterglow electrical discharge region; in which the improvement comprises the construction of said afterglow electric discharge detector system predominantly from a block of machinable radiation transparent material, into which block is machined a multiplicity of holes, each of said holes serving to form an afterglow electrical discharge region.

8. An afterglow electric discharge detector system as in claim 7 in which the inner wall of at least one hole machined into the block of machinable radiation transparent material is lined.

9. An afterglow electric discharge detector system as in claim 7 in which the block of machinable radiation transparent material is selected from the group consisting of crystalline magnesium fluoride and crystalline lithium fluoride.

10. A method of producing ionized sample comprising the steps of:
 a. obtaining an afterglow electric discharge detector system of the type including an afterglow electrical discharge region with electrodes positioned with respect thereto so as to allow creation of an electric discharge in said afterglow electrical discharge region when electrical energy is applied to said electrodes, which also includes means for allowing sample and carrier gas to be caused to flow through said afterglow electrical discharge region; in which the improvement comprises the construction of said afterglow electric discharge detector system predominantly from a block of machinable radiation transparent material, into which is machined at least one hole, said hole serving to form an afterglow electrical discharge region; and
 b. causing sample and carrier gas to flow through said afterglow electric discharge detector system; and
 c. simultaneously applying electrical energy to the electrodes thereof.

* * * * *